US008835014B2

(12) United States Patent
Wang et al.

(10) Patent No.: US 8,835,014 B2
(45) Date of Patent: Sep. 16, 2014

(54) COATING COMPOSITION FOR SKIN-CONTACTING SURFACE OF ELASTOMERIC ARTICLES AND ARTICLES CONTAINING THE SAME

(75) Inventors: Shiping Wang, Libertyville, IL (US); Yun-Siung Tony Yeh, Libertyville, IL (US); James Owens, Kingsport, TN (US); Wei Cheong Wong, Kedah (MY)

(73) Assignee: Allegiance Corporation, McGaw Park, IL (US)

( * ) Notice: Subject to any disclaimer, the term of this patent is extended or adjusted under 35 U.S.C. 154(b) by 0 days.

(21) Appl. No.: 10/690,653

(22) Filed: Oct. 21, 2003

(65) Prior Publication Data

US 2004/0126604 A1 Jul. 1, 2004

Related U.S. Application Data

(60) Provisional application No. 60/420,200, filed on Oct. 22, 2002.

(51) Int. Cl.
*A61L 31/08* (2006.01)
*A61L 31/10* (2006.01)
*A61L 31/14* (2006.01)
*C08L 5/08* (2006.01)
*A41D 19/00* (2006.01)

(52) U.S. Cl.
CPC ............... *A61L 31/10* (2013.01); *A61L 31/14* (2013.01); *A61L 31/141* (2013.01); *C08L 5/08* (2013.01); *A41D 19/0055* (2013.01); *A41D 2400/32* (2013.01)
USPC ..................... 428/500; 427/385.5; 424/78.02; 514/724

(58) Field of Classification Search
None
See application file for complete search history.

(56) References Cited

U.S. PATENT DOCUMENTS

| 4,105,782 A * | 8/1978 | Yu |
| 4,105,783 A * | 8/1978 | Yu et al. .......... 514/459 |
| 4,186,445 A | 2/1980 | Stager |
| 4,690,825 A | 9/1987 | Won |
| 4,853,978 A * | 8/1989 | Stockum ........... 2/167 |
| 4,873,091 A | 10/1989 | Jankower et al. |
| 4,880,617 A | 11/1989 | Abrutyn |
| 4,898,913 A | 2/1990 | Ziemelis et al. |
| 4,920,158 A * | 4/1990 | Murray et al. ......... 523/111 |
| 4,948,818 A | 8/1990 | Carmody et al. |
| 4,962,133 A | 10/1990 | Chromecek et al. |
| 4,962,170 A | 10/1990 | Chromecek et al. |
| RE33,429 E | 11/1990 | Abrutyn |
| 5,026,781 A | 6/1991 | Ziemelis et al. |
| 5,028,435 A | 7/1991 | Katz et al. |
| 5,035,890 A | 7/1991 | Braun |
| 5,073,365 A | 12/1991 | Katz et al. |
| 5,133,090 A | 7/1992 | Modak |
| 5,135,660 A | 8/1992 | Chromecek et al. |
| 5,135,740 A | 8/1992 | Katz et al. |
| 5,135,989 A | 8/1992 | Ziemelis et al. |
| 5,145,675 A | 9/1992 | Won |
| 5,145,685 A | 9/1992 | Carmody |
| 5,156,843 A | 10/1992 | Leong et al. |
| 5,169,904 A | 12/1992 | Ziemelis et al. |
| 5,208,038 A | 5/1993 | Gressani et al. |
| 5,316,774 A | 5/1994 | Eury et al. |
| 5,357,636 A * | 10/1994 | Dresdner et al. ............... 2/161.7 |
| 5,458,890 A | 10/1995 | Williford et al. |
| 5,547,988 A * | 8/1996 | Yu et al. ......................... 514/557 |
| 5,840,293 A | 11/1998 | Nacht et al. |
| 5,851,538 A | 12/1998 | Froix et al. |
| 5,856,409 A | 1/1999 | Ziemelis et al. |
| 5,869,072 A * | 2/1999 | Berry .............................. 424/402 |
| 5,871,722 A | 2/1999 | Nacht et al. |
| 5,939,085 A | 8/1999 | Jacobs |
| 5,939,453 A | 8/1999 | Heller et al. |
| 5,954,869 A | 9/1999 | Elfersy et al. |
| 5,955,109 A | 9/1999 | Won et al. |
| 5,968,543 A | 10/1999 | Heller et al. |
| 6,001,367 A * | 12/1999 | Bazin et al. .................... 424/757 |
| 6,037,386 A * | 3/2000 | Modak et al. .................. 523/105 |
| 6,060,512 A * | 5/2000 | Yu et al. ......................... 514/558 |
| 6,120,587 A | 9/2000 | Elfersy et al. |
| 6,153,208 A | 11/2000 | McAtee et al. ............... 424/402 |
| 6,261,589 B1 * | 7/2001 | Pearson et al. ............... 424/439 |
| 6,274,154 B1 * | 8/2001 | Chou ............................. 424/402 |
| 6,280,673 B1 * | 8/2001 | Green et al. ................... 264/255 |
| 6,391,409 B1 | 5/2002 | Yeh |
| 6,423,328 B2 | 7/2002 | Chou |

(Continued)

FOREIGN PATENT DOCUMENTS

| GB | 2304573 | 3/1997 |
| JP | 62-085003 | 4/1987 |
| JP | 2007-067906 | 3/1997 |
| JP | 2002-003360 | 1/2002 |
| JP | 2003-027083 | 1/2003 |
| WO | WO93/18745 | 9/1993 |
| WO | WO94/12115 | 6/1994 |
| WO | WO01/08640 | 6/2001 |
| WO | WO02/092046 | 11/2002 |
| WO | WO03/092650 | 11/2003 |
| WO | WO2005/034891 | 5/2005 |

OTHER PUBLICATIONS

MSDS data sheet for Sodium Citrate (dated Feb. 16, 2006).*

*Primary Examiner* — Kevin Bernatz

(57) ABSTRACT

The invention described herein relates to a therapeutic, moisturizing coating composition for elastomeric articles which is applied directly onto the skin-contacting surface of the article as part of the manufacturing process. The coating composition is thermally stable and subsequently hydrates when contacted with a moisturized skin surface to convert into a liquid "lotion" form during wearing of the article. The coating composition provides therapeutic benefits to the wearer's skin as a result of wearing the article, such as improved skin moisturization, softness of feel, improved skin elasticity and firmness, and reduced redness and irritation. The invention is particularly useful in medical gloves, including examination and surgical gloves.

44 Claims, No Drawings

(56) References Cited

U.S. PATENT DOCUMENTS

| | | | |
|---|---|---|---|
| 6,572,874 B1 | 6/2003 | Harrison et al. | |
| 6,630,152 B2 | 10/2003 | Chou | 424/402 |
| 6,673,054 B1* | 1/2004 | Gould et al. | 604/292 |
| 6,692,756 B2 | 2/2004 | Chou | 424/402 |
| 6,953,582 B2* | 10/2005 | Chou | 424/402 |
| 6,967,261 B1* | 11/2005 | Soerens et al. | 602/48 |
| 7,163,674 B2* | 1/2007 | Majeti et al. | 424/70.1 |
| 7,566,502 B1 | 7/2009 | Chen | |
| 2001/0006680 A1* | 7/2001 | Mansouri | 424/499 |
| 2002/0025335 A1* | 2/2002 | Chou | 424/402 |
| 2002/0127256 A1* | 9/2002 | Murad | 424/401 |
| 2003/0017193 A1 | 1/2003 | Chou | 424/443 |
| 2003/0059489 A1 | 3/2003 | Letourneau et al. | |
| 2003/0124202 A1* | 7/2003 | Hahn et al. | 424/722 |
| 2003/0204893 A1* | 11/2003 | Chou | 2/161.6 |
| 2004/0062392 A1 | 4/2004 | Morton | 380/200 |
| 2004/0115250 A1 | 6/2004 | Loo | |
| 2004/0122382 A1 | 6/2004 | Johnson | |
| 2004/0126604 A1* | 7/2004 | Wang et al. | 428/500 |
| 2004/0241201 A1* | 12/2004 | Wang et al. | 424/401 |
| 2005/0042248 A1 | 2/2005 | Ahmad | |
| 2007/0020342 A1* | 1/2007 | Modak et al. | 424/642 |
| 2008/0020023 A1* | 1/2008 | Wang et al. | 424/443 |
| 2010/0035999 A1* | 2/2010 | Pereira et al. | 514/772 |

* cited by examiner

COATING COMPOSITION FOR SKIN-CONTACTING SURFACE OF ELASTOMERIC ARTICLES AND ARTICLES CONTAINING THE SAME

RELATED APPLICATION DATA

This application is based on U.S. Provisional Patent Application Ser. No. 60/420,200 filed on Oct. 22, 2002.

FIELD OF THE INVENTION

The invention relates to the field of medical devices. In particular, the invention relates to a coating composition for skin-contacting surfaces of elastomeric articles.

BACKGROUND OF THE INVENTION

Elastomeric articles which are used in such a manner so as to contact the wearer's skin are well known. Articles such as medical gloves and condoms, for example, are anticipated to be worn by the user for extended period of time. Because certain elastomeric articles are used with relatively higher frequency as well as with prolonged duration, important characteristics of such articles include their physical properties and their comfort of use.

A variety of medical gloves, e.g., surgical gloves and examination gloves, are well known and readily available in the medical field. The chemical and physical properties of elastomers used in such gloves have been researched, and gloves exhibiting desirable properties in accordance with their usage have been developed. Properties such as tensile strength as elongation modulus, as well as coatings and lubricants, which enhance their usage and/or donning characteristics, have been investigated. A variety of elastomeric polymer compositions have been examined as well, including formulations using natural and synthetic latex.

When gloves are worn for extended periods of time, body heat is generated by the hand and heavy perspiration that can cause overhydration damaging the natural skin protection afforded by the stratum corneum. After the gloves are removed from the hand and the sweat evaporates, the skin of the hand can become dry, sensitive and sometimes, infective. Such undesirable skin conditions can lead to even more serious skin problems as a result of the loss of epidemical lipid barrier layer which preserves skin moisture.

Pre-donning skin lotions have been developed for application to the user's skin prior to donning gloves. Such lotions are typically applied separately to the skin, and the glove is then donned afterward. Other lotions are applied to the skin after the glove has been removed. Therapeutic skin-moisturizing gloves containing water-activatable material on a skin-contacting surface are described in Berry U.S. Pat. No. 5,869,072. The water-activatable material disclosed in this reference includes polyvinyl alcohol, as well as additional ingredients such as moisturizers and vitamins and is applied onto a flexible porous sheet which is associated with a glove. Chou U.S. Pat. No. 6,274,154 describes an elastomeric glove wherein the skin-contacting surface contains an aloe vera coating in the dry state. One problem associated with many lotions or creams is the deterioration of glove performance as a result of adverse effects on barrier and physical properties of the elastomer. Another problem associated with pre-coated gloves is their ability to withstand sterilization treatment and/or elevated thermal environments, encountered during the manufacturing process and storage, without adverse impact on either the coating, elastomer properties, or both. Yet another problem with such lotions or creams is the use of oily emollients, which can produce an uncomfortable greasy feeling.

Certain elastomeric articles, such as surgical gloves, are worn for extended periods of time during medical procedures. The comfort, maintenance of skin moisture, and reduction of skin irritation have become of increasing interest in the art. One difficulty associated with developing elastomeric gloves which are both functional and comfortable to the user's skin has been the balancing of their desirable physical (e.g., tactile) attributes in combination with beneficial and therapeutic results for the user's skin. Even more difficult is the accomplishment of these physical and comfort characteristics while at the same time also providing thermal stability and topical therapeutic benefit.

Accordingly, there is a need in the field of skin-contacting elastomeric articles for improvements in their comfort to the user. Particularly advantageous would be the development of an elastomeric glove which is pre-coated with a therapeutic skin care treating composition which is thermally stable. Even more desirable would be such an elastomeric coating layer which provides a non-greasy, comfortable feeling to the skin.

SUMMARY OF THE INVENTION

The invention provides an elastomeric article comprising a therapeutic coating composition on the skin-contacting surface that can be applied to the article during its manufacture and subsequently afford a comfortable and therapeutic effect to the wearer's skin while maintaining the desirable physical properties of the article. It has been discovered that a coating composition can be developed which is compatible with medical gloves, is thermally stable, has no substantial adverse effect on its physical properties, has reduced irritation for the wearer's skin, has a non-sticky and non-greasy feel, has good surface-to-skin transference, and has reduced inter-surface and intra-surface tackiness between like elastomeric articles. Particularly surprising is it has been discovered that not only does the coating composition reduce the adverse effects of wearing elastomeric articles over time, but it improves the condition of the wearer's skin as a result of the wear. Even more surprising is that such a formulation could be developed with a combination of ingredients that can "survive" the conditions of article (e.g., glove) manufacturing processes and equipment, namely the drying or dehydration steps, without significantly diminishing the beneficial properties of the composition as a result. Elastomeric articles with which the invention can be used include industrial gloves, medical gloves (i.e., examination and surgical gloves), condoms, and the like. The invention is particularly useful in examination and surgical gloves.

The invention provides a therapeutic coating composition to be applied to a skin-contacting surface of a skin-contacting elastomeric article, said coating composition comprising a moisturizing agent; and wherein said coating composition is applied directly onto said elastomeric article surface and presented in dry state hydratable form. The therapeutic coating composition hydrates upon moisture contact and transfers onto the wearer's skin during use, providing the topical benefits afforded by the ingredients of the composition.

The coating composition provides therapeutic benefit to the wearer's skin, such as skin moisturization, which is "activated" by moisture on the wearer's skin. The moisture from the wearer's skin converts the coating composition into a hydrated, liquid "lotion" form, and the "lotion" form is transferred directly from the skin-contacting surface of the article onto the wearer's skin while worn. The coating composition continues to provide prolonged therapeutic benefit to the skin following its removal. The coating composition is chemically compatible with the elastomeric materials, and has no substantial impact on the physical properties of the article. The coating composition of the invention is thermally stable and survives elevated temperatures associated with manufacturing and certain sterilization treatments. The coating composition has a pleasant non-sticky, non-greasy feel. Additional ingredients can be combined with the composition of the invention, such as lubricants, anti-tacking agents, antimicrobial agents and time release or sustained release agents as well.

An important aspect of the coating composition of the invention is the collective skin moisturization efficacy of multiple coating composition ingredients. The therapeutic skin properties of the coating composition are accomplished in part by the discovery that some of the ingredients possess dual functionalities, wherein at least one of their functions is beneficial skin moisturization. The moisturizing functionality of the coating composition is premised upon at least two of the following moisturization effects. First, some of the ingredients of the composition function as water-soluble moisturizers, such as glycerine and sorbitol. Second, some of the ingredients function as skin penetrative moisturizers, such as panthenol. Third, some ingredients can function as prolonged skin surface moisturizers, such as film-forming polymers such as chitosan. Furthermore, combinations of the above can be employed to suit the nature of wear associated with different elastomeric article types. For example, since examination gloves are worn for relatively shorter time periods, the prolonged skin surface moisturizer(s) used can be optional.

The invention provides a coating composition for skin-contacting surfaces of elastomeric articles comprising at least one polyhydric alcohol moisturizer and at least one alphahydroxy lactone, wherein the composition is water-soluble and hydratable upon contact with skin. Preferred polyhydric alcohol moisturizers are glycerol, sorbitol and pantothenol. A preferred alphahydroxy lactone is gluconolactone.

The invention also provides an elastomeric article comprising a coating composition on the skin-contacting surface, the coating composition being in the dry state and comprising at least one polyhydric alcohol moisturizer and at least one alphahydroxy lactone, wherein the composition is water-soluble and hydratable upon contact with skin. Of particular interest are elastomeric articles that are typically worn for periods of time sufficient to allow the coating composition to have its effect on the wearer's skin, such as examination and surgical gloves.

The invention provides a process for making a skin-contacting elastomeric article providing enhanced therapeutic properties to the skin of the wearer, the process comprising: applying a coating composition to the skin-contacting surface of the elastomeric article, the coating composition comprising at least one polyhydric alcohol moisturizer and at least one alphahydroxy lactone, wherein the composition is water-soluble and hydratable upon contact with skin; and drying the composition on the skin-contacting surface of the article. The process can be used in the manufacture of examination and surgical gloves.

The invention further provides a method of therapeutically treating the skin on the hands of an individual in need of said treatment comprising the steps of: providing an elastomeric glove comprising a dry-state coating composition comprising at least one polyhydric alcohol moisturizer and at least one alphahydroxy lactone, wherein the composition is water-soluble and hydratable upon contact with skin; donning the glove on the hand; wearing the glove for a period of time sufficient to permit hydration and transfer of the coating composition onto the skin surface of the hand; and subsequently removing the glove from the hand. The therapeutic treatments include improved skin moisturization, reduced flaking, softness of feel, improved skin elasticity and firmness, reduced redness and irritation, and reduced appearance of wrinkles.

Additional embodiments and advantages of the invention will become apparent from the following description.

DETAILED DESCRIPTION OF THE INVENTION

The term "therapeutic" is meant to refer to the effect of improving skin-related properties of moisture, elasticity, comfort, non-irritation, preservation of protective skin barrier properties, and the like.

The term "hydratable" as used herein refers to the property in which liquids interact with the coating composition to facilitate conversion into a more liquid form thus facilitating the transfer of the composition to the skin. The term is used relative to "dry state", which is used herein to indicate the substantial absence of moisture or water.

As used herein, the term "thermally stable" and "thermal stability" when referring to the properties of the coating composition of the invention is meant to indicate that the coating composition in the dry state can withstand elevated temperatures of about 70° C.

The coating composition according to the invention is adapted for application directly onto a skin-contacting surface of an elastomeric article as part of the manufacturing process. The coating composition of the invention is particularly suited for elastomeric articles which include, as part of their anticipated usage, intimate contact with a wearer's skin surface and prolonged residence thereon. Suitable skin-contacting elastomeric articles include, but are not limited to, gloves (e.g., industrial, medical and surgical gloves), condoms, finger cots, and the like. Elastomeric articles per se to be treated according to the invention can be manufactured using conventional techniques and equipment readily available to those skilled in the art. For example, elastomeric gloves can be made using conventional former-dipping-curing techniques and equipment, such as that described in Yeh, U.S. Pat. No. 6,391,409, the entire text of which is incorporated herein by reference.

Elastomers or elastomeric substrates upon which the coating composition can be applied can include any natural or synthetic elastomeric polymer which is chemically compatible with the coating composition ingredients and appropriate for the intended use, e.g., surgical environment. Suitable elastomers include, but are not limited to, synthetic and natural rubber latex. Natural rubber that can be used includes rubber made from hevea rubber latex and guayule rubber latex. Synthetic rubber polymers which can be used include nitrile rubber, polyurethane, polyisoprene, polychloroprene, styrene block co-polymers and polymer blends thereof. Synthetic rubbers that can be used also include acrylic diene block co-polymerr, acrylic rubber, butyl rubber, EPDM rubber, polybutadiene, chlorosulfonated polyethylene rubber and fluororubber.

One important characteristic of the invention is that the coating composition can be dried directly onto the surface of the article as part of the manufacturing process. The coating composition is packaged, stored and presented in a dried state on the article surface. Thus, when in intimate contact with a moisturized skin surface the coating composition converts into a liquid "lotion" form during wear. It is during this stage that the coating composition transfers and provides an initial therapeutic and moisturizing benefit to the wearer which remains on the skin surface for a period of time after the article is removed.

Water-soluble moisturizers that can be used in the coating composition include polyhydric alcohol emollients and/or moisturizers. At least one moisturizer is present, but combinations of two or more moisturizers can be use as well. Suitable polyhydric alcohol moisturizers that can be used include, but are not limited to, glycerin and sorbitol. Preferably, combination of glycerin and sorbitol is used. An example of glycerin or 1,2,3-propanetriol that can be used is Glycon™ G 300 (available from Aldrich Chemical Company, Milwaukee, Wis.). One example of sorbitol or D-glucitol that can be used is available from Aldrich Chemical Company, Milwaukee, Wis.

Water-soluble moisturizer ingredients can be present in an amount up to about 3.00% by weight of the total composition. Preferably, water-soluble moisturizer is present in an amount ranging from about 0.10% to about 1.50%. Glycerin as a water-soluble moisturizer can be present individually in an amount ranging from about 0% to about 3.00% by weight, preferably from about 0.10% to about 1.50%. Sorbitol as a water-soluble moisturizer can be present individually in an amount ranging from about 0% to about 3.00%, preferably from about 0.10% to about 1.50% by weight.

Additional moisturizing agents can be used in conjunction with the above-described polyhydric alcohols. The additional moisturizing agents can likewise be polyhydric alcohols. Preferably, the composition of the invention comprises pantothenol or 2,4-dihydroxy-N-(3-hydroxypropyl)-3,3-dimethylbutanamide (a.k.a. pro-vitamin B), which, in vivo, increases topical moisture retention thereby prolonging elasticity and suppleness of the skin, reduces inflammation and irritation of the skin, and stimulates epithelization. Suitable pantothenol for use in the invention is available from Aldrich Chemical Company, Milwaukee, Wis. and Daiichi Fine Chemicals, Japan, as well as Ritapan™ DL (available from RITA Corporation, Woodstock, Ill.).

The pro-vitamin B form, pantothenol, is preferred for use in the composition. Pantothenoic acid, the acid form of pantothenol, is a member of the B-complex vitamins and is also a structural component of acyl carrier proteins (ACP) as an essential component of fatty acid synthetase complex. The stability of pantothenoic acid is, however, highly sensitive to pH fluctuations. The pro-vitamin form pantothenol is preferred because it is more stable and easily absorbed, and converts into the acid form in vivo. Additional moisturizing agents such as pantothenol can be present in an amount ranging from about 0.10 to about 3.00%, preferably from about 0.30% to about 0.50% by weight of the total composition.

The coating composition can further comprise a hydroxyacid as a skin exfoliant. Hydroxyacids enhance proliferation of skin cells and increases ceramide biosynthesis keratinocytes, regulates epidermal thickness and improves desquamation resulting in smoother skin and youthful appearance. Suitable hydroxyacids that can be used include monocarboxylic acids, dicarboxilic acids and polyhydroxy acids, and their intramolecular lactones, esters and salt forms. Examples of monocarboxilic acids include both alpha and beta forms. Gluconolactone or D-glucono-1,5-lactone is preferred because it provides a therapeutic effect with relatively less skin irritation. One example of gluconolactone that can be used is Glucono-delta-Lactone available from Daniels Archer Midland/DL, United Kingdom or Jungbunzlauer, Newton Center, Massachusettes. Hydroxyacid(s) such as gluconolactone can be present in an amount ranging from about 0.10% to about 3.00%, preferably from about 0.10% by weight to about 0.50% by weight of the total composition.

A variety of additional functional, therapeutic and cosmetic additives can be included in the coating composition of the invention as, well, provided they are water-soluble and do not adversely affect the chemical and physical properties of the composition. Advantageous functional additives which enhance the properties of the coating composition that can be used in the coating formulation include pH adjusters, anti-tack agents, donning agents and hydration promoters.

Donning agents that can be used include damp donning agents and dry donning agents, and combinations thereof. Damp donning agents that can be used include quaternary ammonium halide salts which additionally exhibit antimicrobial properties. A preferred quaternary ammonium halide salt is cetylpyridinium chloride or 1-hexadecylpyridinium chloride. One example of cetylpyridinium which can be used is CPC available from Zeeland Chemicals, Zeeland, Mich.

Dry donning agents that can be used in the coating composition include silicone-based compounds, including polyalkylsiloxanes. One example of a polyalkylsiloxane that can be used is polydimethylsiloxane dispersion, such as GE SM 2140™ (available from GE Silicones, Waterford, N.Y.). Other silicone-related dry donning agents can be used that also function as skin protecting agents as well, such as dimethicone.

Damp donning agents such as cetylpyridinium chloride can be present in an amount ranging from about 0.10% to about 2.00%, preferably from about 0.10% to about 1.80% by weight of the total composition. Dry donning agents can be present in an amount ranging from about 0.10% to about 8.00%, preferably from about 0.10% to about 0.25% by weight of the total composition.

The coating composition can also include a pH adjuster, which can be an inorganic acid, organic acid, or combination thereof. The amount of pH adjuster to be added will, of course, vary but is preferred that the compound and amount be selected to adjust the pH value to from about pH 4 to about pH 7 range. Preferred are non-irritating pH adjusters, such as citric acid or 2-hydroxy-1,2,3-propane-tricarboxylic acid, which is available from Aldrich Chemical Company, Milwaukee, Wis., for example. The pH adjuster(s) such as citric acid can be present in an amount ranging from about 0% to about 0.50% by weight of the total composition.

Anti-tack agents that can be used in the coating composition include silicones such as silicone oil, silicone resins, silicone gums and silicone elastomers, cationic polymers such as polydiethyldimethyl ammonium chloride, fatty acid salts and esters such as potassium stearate and trimethylolpropane triisostearate, carboxylic ester of hydroxyalkylamide such as erucamide, fluoro-compounds such as PTFE (polytetrafluoroehtylene) and phosphate salts such as ammonium alkyl phosphate (such as Darvan L™ available from R.T. Vanderbilt, Norwalk, Conn.). Anti-tack agent(s) can be present in an amount ranging from about 0.25% to about 2.50% of the total weight of the composition.

The coating composition of the invention preferably contains a hydration promoter to facilitate uptake and absorption of topical moisture (water) need to "activate" the coating composition. Preferred hydration promoters include those which additionally function as buffers to a acidic pH adjuster when present, such as sodium citrate. One example of suitable sodium citrate that can be used is sodium citrate or 1,2,3-propanetricarboxylic acid trisodium salt, such as sodium citrate dihydrate available from Aldrich Chemical Company, Milwaukee, Wis. Hydration promoter(s) such as sodium citrate can be present in an amount ranging from about 0% to about 2.00%, preferably from about 0% to about 0.50% by weight of the total composition.

Other therapeutic and cosmetic agents can be used as well, such as "anti-aging" compounds. Cosmetic agents that can be used include retinol, and/or those that can also function as exfoliants, such as alpha hydroxy lactones, such as gluconolactone. Fragrances and coloring agents can also be used in the coating formulation to render the composition more appealing to the user.

As a further embodiment, the coating composition can comprise a plasticizer to facilitate uniform distribution of the water-soluble film forming polymer. Preferred plasticizers include esters such as triethyl citrates, because of its additional chemical function as a buffer in the formulation. One example of suitable triethyl citrate or 1,2,3-propanetricarboxylic acid, 2-hydroxy-, triethyl ester is Hydagen™ CAT available from Cognis, Cincinnati, Ohio. Plasticizer(s) such as Hydagen™ CAT can be present in an amount ranging from about 0% to about 1.00%, preferably from about 0% to about 0.50% by weight of the total composition.

In the liquid state prior to application to the surface of the elastomeric article, the coating composition further includes water, preferably deionized water. The initial coating composition is applied to the surface in liquid state, and can be applied using a variety of coating techniques. Suitable coating techniques include dipping and spraying. The coating composition is subsequently dried directly onto the article surface as part of the manufacturing process. Application and drying techniques that can be used in accordance with the invention include the tumbling process and the spraying process.

According to one aspect of the invention, the coating composition is applied to the article surface and dried directly on the skin-contacting surface of the article. In general, the coating composition of the invention can be applied to gloves using the tumbling method or spray method. The spraying method is preferred for preparing surgeon's or surgical gloves. The tumbling method is preferred for preparing examination gloves. The Examples contain descriptions of each of these processes in greater detail.

The spray method is a process that applies the coating composition onto the glove using a spraying apparatus. In this process, the gloves are placed into a tumbler including a spraying device. The coating composition is sprayed in liquid sate in multiple and non-continuous steps. Heat is applied during spraying and tumbling to dry the lotion onto the glove surface.

Alternatively, the tumbling method is a process that applies the coating composition in liquid state onto the glove surface by placing the gloves into a tumbler and then filling the tumbler with the coating composition liquid. The gloves are then tumbled or washed. A tumbling process that can be used, for example, can be similar to that described in Chen et al. U.S. patent application Ser. No. 10/666,650 filed Sep. 17, 2003, now pending.

An important aspect of the coating composition of the invention is the collective skin moisturization efficacy of multiple coating composition ingredients, and some of the coating composition ingredients of the invention can possess dual functionality. The humectant functionality of the coating composition is premised upon at least two of the following moisturization effects. First, some of the ingredients of the composition function as water-soluble moisturizers, such as glycerine and sorbitol. Second, some of the ingredients function as skin penetrative moisturizers, such as pantothenol. Third, some ingredients can function as prolonged skin surface moisturizers, such as film-forming polymers such as chitosan. Furthermore, combinations of the above can be employed to suit the nature of wear associated with different elastomeric article types. For example, since examination gloves are worn for relatively shorter time periods, the prolonged skin surface moisturizer(s) used can be optional.

Variations of the above ingredients and the addition of other ingredients are possible in accordance with the invention, provided the therapeutic effect of the formulation on the skin is not significantly comprised. The ingredients of the coating composition, when combined, must be capable of participating in the therapeutic, moisturizing, non-irritating, moisturizing effect on the wearer's skin.

When the elastomeric article is intended for extended wear, such as a surgeon's glove, the coating composition preferably further comprises a water-soluble film forming polymer. Suitable water-soluble, film forming polymers which can be used include natural or synthetic water soluble, film forming polymers. Preferred are cationic water-soluble film forming polymers. Suitable film forming polymers which can be used in accordance with the invention include, but are not limited to, cellulose and cellulose derivatives, polyvinyl pyrrolidone (PVP) and polyvinyl pyrrolidone derivatives, and polysaccharides. Preferably, polysaccharides are used as the water-soluble film forming polymer, and most preferred as the film forming polymer is chitosan.

Chitosan can be prepared from naturally occurring chitin, which can be obtained from crustacean and insect exoskeletal material. Chitosan is also referred to as deacetylated chitin, poly-D-glucosamine, poliglusam, beta-1,4-poly-D-glucosamine, and beta-(1,4)-2-amino-2-deoxy-D-glucose. Chitosan and its derivatives can be used in accordance with the invention. One source of chitosan which can be used is deacetylchitin, available as Hydagen™ CMF from Cognis, Cincinnati, Ohio. When present, film forming polymer(s) such as chitosan can be present in an amount up to 1.00%, preferably ranging from about 0.05% to about 0.20% by weight of the total composition.

Water, preferably deionized water, can be present in an amount ranging from about 92% to about 99.5% by weight of the total composition. Total solids content of the formulation, or TSC, can also vary from about 0.50% to about 8.00%. Overall, variations of the proportions and amounts of the ingredients can be adjusted provided such modifications do not substantially compromise the desired properties of the resulting formulation according to the invention.

In another embodiment, particle technology can also be used in conjunction with the coating composition to further enhance the collective benefits and properties of the invention. In particular, microporous particles can be included in the formulation to provide a number of additional properties, such as sustained release or time release of ingredients. Preferably, the microporous particles that can be used are those embedded with skin care ingredients that can be incorporated into a powder-free polymer coating. Microporous particle technology that can be used as a component of the coating composition of the invention includes that which is described in U.S. Pat. No. Reissue No. 33,429, U.S. Pat. No. 4,873,091, U.S. Pat. No. 4,690,825, U.S. Pat. No. 5,028,435, U.S. Pat. No. 5,035,890, U.S. Pat. No. 5,968,543, U.S. Pat. No. 5,955,109, U.S. Pat. No. 5,073,365, U.S. Pat. No. 5,135,740, U.S. Pat. No. 5,145,675, U.S. Pat. No. 5,145,685, U.S. Pat. No. 5,156,843, U.S. Pat. No. 5,316,774, U.S. Pat. No. 5,458,890, U.S. Pat. No. 5,840,293, U.S. Pat. No. 5,871,722, and U.S. Pat. No. 5,851,538, the entire texts of which are incorporated herein by reference. One particular microsponge particle of interest is Microsponge 5700 (available from Cardinal Health, Inc., Somerset, N.J.), which can controllably release particle-absorbed dimethicone by diffusion, moisture, pH, friction, temperature, and/or other active ingredients.

The coating composition of the invention can further contain additional beneficial ingredients provided such are chemically compatible with the composition of the invention and do not adversely affect the desired therapeutic properties of the composition. Additional ingredients that can be included in the coating composition include, but are not limited to, antimicrobial agents, anti-inflammatory agents, topical cleansing agents, anti-perspiration agents, and the like.

The coating composition of the invention can also be applied to elastomeric article surfaces using conventional equipment and techniques readily available to those skilled in the field of manufacturing elastomeric articles, including on-line and off-line techniques such as dipping, spraying, tumbling, and the like. For preparing a coated surgeon's glove, the preferred method of application is off-line spraying. For the preparation of a coated exam glove, the preferred on-line method of application is dip coating, and the preferred off-line method is the tumbling method of coating.

Using a surgeon's glove as an example, the user removes the glove from a dispenser or package. Prior to donning the glove, the user typically scrubs their hands with surgical scrub solution followed by rinsing with water. After wiping their hands dry with a sterile towel, the user dons the glove by placing the hand into the glove such that the glove generally conforms to the shape of the user's hand. At this point, the water-based moisture from the user's skin interacts with the coating composition thereby hydrating the composition and converting it into a liquid "lotion"-type phase. Upon hydration of the coating composition, the comfort and therapeutic benefits such as moisturization of the skin, become realized. Furthermore, after removal of the glove, the coating composition remains on the user's skin thereby providing continued therapeutic benefit to the skin.

The following examples further illustrate the invention. Unless otherwise noted, w/w % is meant to indicate percent dry weight of the total weight.

Example 1

Preparation of Coating Composition for Surgical Gloves

A coating composition in accordance with the invention was prepared by initially determining the amount of each ingredient desired using conventional ingredient amount calculation methods.

After the amount of ingredients has been determined, the total amount of water was added to a beaker and continually stirred as each of the ingredients were added. The composition was stirred at ambient temperature for at least about one hour until a stable, homogenous solution was formed. The pH and viscosity of the composition were measured in accordance with ASTM E70-97 (Standard Test Method for pH of Aqueous Solutions with the Glass Electrode) and ASTM D5225-98 (Standard Test Method for Measuring Solution Viscosity of Polymers with a Differential Viscometer). Using these methods, the pH was between 4.8 and 6.0, and the viscosity was measured at between 15 and 45 cps at room temperature using a spindle no. 4 at 60 rpm. The resulting composition was then deposited into a glass container and sealed with a lid.

The resulting liquid coating formulation had the following composition:

| Formula 1: | |
| --- | --- |
| Ingredient: | Amount (w/w %) |
| Chitosan | 0.10 |
| Citric acid | 0.08 |
| Glycerin | 0.15 |
| Sorbitol | 0.50 |
| Pantothenol | 0.30 |
| Gluconolactone | 0.15 |
| Triethyl citrate | 0.30 |
| Cetylpyridinium chloride | 1.00 |
| Silicone dispersion | 0.20 |
| Sodium citrate | 0.40 |
| Deionized water | 97.22 |
| Total: | 100 |

TSC (total solids content) = 2.70%

Chitosan and triethyl citrate were obtained from Cognis, Cincinnati, Ohio. Citric acid, glycerin, sorbitol, pantothenol and sodium citrate were obtained from Aldrich Chemical Company, Milwaukee, Wis. Gluconolactone was obtained from Jungbunzlauer, Newton Center, Massachusettes. Cetylpyridinium chloride was obtained from Zeeland Chemicals, Zeeland, Mich. Silicone was obtained from GE Silicones, Waterford, N.Y.

Example 2A

Preparation of Coated Glove (Spraying Method)

A surgeon's glove containing a coating composition on the skin-contacting surface can be prepared as follows:

The uncoated glove can be prepared in accordance with conventional glove forming techniques and equipment. For instance, a former in the shape of a glove is provided and coated with a coagulant composition and subsequently dried. The coagulant-coated former is then dipped into polyisoprene latex to coat the former and the latex is leached with water, coated with a powder layer and cured on the coated former. After curing, the polyisoprene glove is rinsed, dried and stripped from the former.

Prior to coating, the gloves can be turned inside-out and pre-rinsed and chlorinated using a chlorinator with chlorine solution with a chlorine strength of about 300 ppm to about 1000 ppm. After chlorination, the gloves can be post-rinsed prior to coating.

To coat the glove, the chlorinated gloves are removed from the chlorinator, turned inside out such that the skin-contacting surface is exposed and placed in a tumbler equipped with a spray nozzle. The gloves are then dried for a sufficient period of time.

Tumbler design is an important aspect of the preparation of the gloves in order to ensure even uniform coating of the glove surface. For example, a drum having a diameter of about 43 inches and a total length of about 25 inches can have a total perforated area of about 11.5 inches and a remaining non-perforated area of about 13.5 inches relative to drum length. The non-perforated area of the drum is determined so that some of the gloves to be placed within remain in the non-perforated area for lubrication and so that suction air flow is reduced in the area. The revolution speed can vary. For example, a revolution speed ranging from about 25 rpm to about 35 rpm can be used, preferably from about 31 rpm to about 32 rpm.

Initial drying can be conducted at a temperature of about 32° C. increasing to about 50° C., for a period of about 15 minutes. The first spraying can commence after 15 minutes of tumbling. After the first spraying, the gloves are then tumbled for an additional 60 seconds, and subjected to a second spraying for about 170 seconds and tumbled again for an additional 60 seconds thereafter. A third spraying is applied for about 170 seconds, followed by tumbling at a temperature of about 60° C. for a period of about 2 minutes of cooling. The spraying step can be repeated until the desired amount of coating has been applied to the gloves prior to 25 minutes heat tumbling and 2 minutes cooling cycle.

At the conclusion of the tumbling stage, the gloves can be removed from the tumbler for the turning stage. During the turning process, the gloves are manually turned inside out and then subjectwed to the final drying at a temperature of about 55 C for a period of about 15 minutes. The gloves are then allowed to cool for a period of about 3 minutes. e gloves are then dried at a temperature of about 34° C. for a period of about 20 minutes. The gloves containing the coating composition in dry-state can then be packaged and sterilized.

Example 2B

Preparation of Coated Glove (Tumbling Method)

An examination glove containing a coating composition on then skin-contacting surface can be prepared as follows:

Prior to coating, the gloves can be post-processed by chlorination. First, the gloves can be turned inside-out exposing the skin-contacting surface and placed into the chlorinator. The glove can then be pre-rinsed and chlorinated using a chlorinbated solution with a chlorine strength of about 400 ppm to about 700 ppm. After chlorination, the gloves can be post-rinsed prior to coating.

For coating, the chlorinated gloves can be removed from the chlorinator and placed into a tumbler for lotion coating and heat drying steps. Excessive water is removed from the gloves by spinning the gloves for a period of about 5 minutes. The tumbler is then filled with an aqueous lotion solution such as per Example 3, Formula 2 or Example 4, Formula 3. The gloves can then be tumbled in the composition for a period of about 10 minutes. The composition can then be drained from the tumbler.

The gloves can then be dried in the tumbler in a heating cycle at a temperature of about 30° C. for a period of about 30 minutes, and subsequently cooled in a cool-down cycle for a period of about 5 minutes. The gloves can then be removed from the tumbler and manually turned inside-out. The gloves can then be dried again in a dryer at a temperature of about 60° C. for a period of about 60 minutes and then allowed to cool to room temperature for about 10 minutes.

In the preparation of coated articles mentioned in the following examples, the processes used to prepare coated articles used a process similar to Example 2B for examination gloves and Example 2A for surgeon's gloves. One of ordinary skill in the art can make adjustments and modifications to the above process parameters as appropriate for particular circumstances.

Example 3

Lotion Formulation for Natural Rubber Examination Glove

| Formula 2: | |
|---|---|
| Ingredient | Amount (% w/w) |
| Citric acid | 0.10 |
| Glycerin | 0.10 |

-continued

| Formula 2: | |
|---|---|
| Ingredient | Amount (% w/w) |
| Sorbitol | 0.30 |
| Pantothenol | 0.20 |
| Gluconolactone | 0.20 |
| Sodium citrate | 0.40 |
| Silicone dispersion | 0.12 |
| Alkyl phosphate ammonium salt | 0.74 |
| Water | 97.84 |
| Total: | 100.00 |

TSC (total solids content, actual) = 2.00%

Citric acid, gluconolactone and sodium citrate were obtained from Jungbunzlauer, Newton Center, Massachusettes. Glycerin and sorbitol were obtained from Aldrich Chemical Company, Milwaukee, Wis. Pantothenol was Ritapan™ DL obtained from Daiichi Fine Chemical, Japan. Silicone was obtained from GE Silicones, Waterford, N.Y. Alylphosphate ammonium salt was obtained from R.T. Vanderbilt, Norwalk, Conn.

Example 4

Lotion Formulation for Powder-Free Nitrile Examination Glove

| Formula 3: | |
|---|---|
| Ingredient | Amount (% w/w) |
| Citric acid | 0.10 |
| Glycerin | 0.10 |
| Sorbitol | 0.30 |
| Pantothenol | 0.20 |
| Gluconolactone | 0.20 |
| Trisodium Citrate | 0.40 |
| Silicone dispersion | 0.12 |
| Alkyl phosphate ammonium salt | 0.48 |
| Water | 98.10 |
| Total: | 100.00 |

TSC (total solids content, actual) = 1.75%

Citric acid, gluconolactone and trisodium citrate were obtained from Jungbunzlauer, Newton Center, Massachusettes. Glycerin and sorbitol were obtained from Aldrich Chemical Company, Milwaukee, Wis. Pantothenol was Ritapan™ DL obtained from Daiichi Fine Chemical, Japan. Silicone dispersion used was GE SM2140 @ 50% (liquid) from GE Silicones, Waterford, N.Y. The alkyl phosphate ammonium salt was Darvan™ L @ 80% (liquid) from R.T. Vanderbilt, Norwalk, Conn.

Example 5

Lotion Formulation for Lotion Polyisoprene Surgeon's Gloves

| Formula 4: | |
|---|---|
| Ingredient: | Amount (% w/w) |
| Chitosan | 0.10 |
| Citric acid | 0.10 |
| Glycerol | 0.25 |
| Sorbitol | 0.75 |
| Pantothenol | 0.50 |
| Gluconolactone | 0.25 |
| Triethyl citrate | 0.50 |
| Cetylpyridinium chloride | 1.00 |
| Silicone dispersion | 0.25 |
| Sodium citrate dihydrate | 0.40 |
| Alkyl phosphate ammonium salt | 1.00 |
| Water (soft) | 94.90 |
| Total: | 100.00 |

TSC (total solids content, actual) = 4.10%

Citric acid, glycerol, sorbitol and sodium citrate dihydrate were obtained from Aldrich Chemical Company, Milwaukee, Wis. Silicone dispersion used was GE SM2140™ @ 50% (liquid) from GE Silicones, Waterford, N.Y. Gluconolactone was obtained from Daniels Archer Midland, United Kingdom. The alkyl phosphate ammonium salt was Darvan™ L @ 80% (liquid) from R.T. Vanderbilt, Norwalk, Conn. Cetylpyridinium chloride was CPC from Zeeland Chemicals, Zeeland, Mich. Chitosan (Hydagen™ CMF) and Triethyl citrate (Hydagen™ CAT) were obtained from Cognis, Cincinnati, Ohio. Pantothenol was Ritapan™ DL obtained from Daiichi Fine Chemical, Japan.

Example 6

Lotion Formulation for Lotion Natural Rubber Surgeon's Gloves

| Formula 5: | |
|---|---|
| Ingredient: | Amount (% w/w) |
| Chitosan | 0.10 |
| Citric acid | 0.10 |
| Glycerol | 0.25 |
| Sorbitol | 0.75 |
| Pantothenol | 0.50 |
| Gluconolactone | 0.25 |
| Triethyl citrate | 0.50 |
| Cetylpyridinium chloride | 1.00 |
| Silicone dispersion | 0.50 |
| Sodium Citrate | 0.40 |
| Alkyl phosphate ammonium salt | 1.00 |
| Water (soft) | 94.65 |
| Total: | 100.00 |

TSC (total solids content, actual) = 4.5%

Chitosan (Hydagen™ CMF) and triethyl citrate were obtained from Cognis, Cincinnati, Ohio. Pantothenol was Ritapan™ DL obtained from Daiichi Fine Chemical, Japan. Citric acid, glycerol, sorbitol and sodium citrate were obtained from Aldrich Chemical Company, Milwaukee, Wis. Cetylpyridinium chloride used was CPC from Zeeland Chemicals, Zeeland, Mich. Silicone dispersion used was Silicone SM2140™ from GE Silicones, Waterford, N.Y. Alkyl phosphate ammonium salt used was Darvan L™ available from R.T. Vanderbilt, Norwalk, Conn.

Various factors affect the appropriate amount (load level) of coating composition applied to the glove, such as glove temperature, composition temperature, number of sprays, distance of glove from spray nozzle, total solids content of composition. The amount of coating (lotion per glove) can be calculated from total lotion spray and load size (number of gloves). Sprayer settings also affect the coating process, including cylinder pressure, liquid pressure, air pressure, and air cap type. Adjustments to appropriate or optimal manufacturing parameters can be selected by those skilled in the glove manufacturing field.

Since the coating composition of the invention is thermally stable, drying and sterilization techniques can be performed on the coated article or glove. As a result of the coating composition being on the article surface in the relatively dry state, the composition of the invention can also accompany the article through certain sterilization treatments without significant adverse effects to either the coating composition properties or elastomer physical and barrier properties. Thus, the coating composition, having therapeutic and moisturizing benefits, can be packaged, stored and initially presented to the user in the dry state on the article surface. A further benefit associated with the coating composition is shelf life and storage longevity, since the dry coating formulation is less susceptible to chemical breakdown or denaturing when stored for relatively extended periods of time.

Therapeutic Effect of Coating Composition:

The follow examples relate to comparative skin property data demonstrating the topical and therapeutic advantages and benefits associated with the gloves prepared in accordance with the invention. There are two main collections of comparative studies involving 1) synthetic (nitrile) examination gloves, and 2) synthetic (polyisoprene) surgeon's gloves. Test Article A for synthetic examination gloves evaluation were prepared in accordance with the invention using the coating composition of Example 4, Formula 3 and applied to the article surface using the tumbling method. Test Article A for synthetic surgeon's gloves evaluation were prepared in accordance with the invention using the coating composition of Example 5, Formula 4 and applied to the article surface using the spray method.

Synthetic Examination Gloves

I. Clinical Evaluation

Gloves prepared in accordance with the invention were clinically evaluated for a variety of skin properties. In each of the following examples, two types of gloves were tested. Test Article A was a synthetic Powder-free Nitrile Examination Lotion Glove prepared according to the invention using the coating composition as found in Example 4, Formula 3 (TSC=1.75%) and process similar to that of Example 2B. Control Test Article B, the comparator glove, was Flexam Nitrile T Ambi™ Glove (available from Cardinal Health, Inc., Dublin, Ohio) untreated with the lotion of the invention. Thirty-one subjects, male and female, were pre-screened for dry skin on the hands following a 36-48 hour "wash out" period, in which the hands were washed daily with Neutrogena® Glycerin Bar and without the use of any moisturizing products on their hands. Twenty-six subjects were selected varying in age from 29 to 58 years. No adverse events were reported during the study. Each subject was equilibrated in a controlled environment for thirty minutes prior to baseline measurements. Baseline measurements were taken of the subjects' hands corresponding to the various testing methods to be applied: NOVA™ meter readings (NOVA™ DPM 9003™, NOVA Technology Corporation, Portsmouth, N.H.) for skin surface moisturization; Chroma Meter™ (CR 300™ from Minolta Corporation, New Jersey) readings for skin redness; TEWL (transepidermal water loss) measurements (TewaMeter™ TM 210 Courage, Khazaka Electronic GmbH, Koln, Germany) for barrier function; and D-Squame™ Skin Sampling Discs for skin smoothness and flakiness.

Each of the twenty-six subjects were give one test glove to be worn on one hand, and a comparator glove to be worn on the other hand for twelve successive 15-minute wear periods, with approximate five-minute rest periods between under observation. Subsequent to the final wear period, the subjects had a three-hour rest period and were then equilibrated for thirty minutes. All baseline measurements were repeated on each subject.

Example 7

Comparative Data—Skin Moisturization

The percent change from baseline NOVA™ measurements to final were taken of the subjects using NOVA™ meter readings (NOVA™ DPM 9003™, NOVA Technology Corporation, Portsmouth, N.H.) to evaluate skin surface moisturization. The results were averaged for both Test Articles A and B and are set forth in the following table:

TABLE 1

| NOVA ™ Percent (%) Change | | |
|---|---|---|
| | Test Article A | Test Article B (control) |
| % Change | 12.60% | 10.74% |

As can be seen from the above data, Test Article A of the invention exhibited a greater percent NOVA™ change value from baseline of 12.60% as compared to Test Article B, the control value of 10.74%. Accordingly, the glove prepared according to the invention increases skin moisturization (1.86%) from wear as compared to non-treated gloves.

Example 8

Comparative Data—Dryness

Each of the subjects' hands (dorsal surface) were evaluated for redness using a Chroma Meter™ (CR 300™ from Minolta Corporation, New Jersey). Readings were taken for each of test Articles A and Test Articles B. The readings for each test article were averaged and are set forth in the following table:

TABLE 2

| Chroma-Meter Percent Change | | |
|---|---|---|
| | Test Article A | Test Article B (control) |
| % Change | 0.13% | 1.27% |

The results demonstrate that the Chroma Meter detected almost no change between the baseline measurements and final measurements, indicating that Test Article A of the invention did not significantly increase redness on the wearer's skin. Therefore, gloves of the invention cause no significant redness of the wearer's hands, in contrast to untreated gloves.

Example 9

Comparative Data—Transepidermal Water Loss

The subjects' hands were measured for baseline and final TEWL (transepidermal water loss), the measurements for which were obtained using a TewaMeter™ 210 Courage (Khazaka Electronic GmbH, Koln, Germany). The readings were averaged and the percent change calculated from the resulting data, as set forth in the following table:

TABLE 3

| TEWL Percent Change | | |
|---|---|---|
| | Test Article A | Test Article B (control) |
| % Change | −0.63% | −7.18 |

The above results demonstrate that Test Article B caused significantly greater transdermal water loss and Test Article A of the invention did not cause significant water loss during wear time of the gloves. As transepidermal water loss is correlated to skin barrier protection, the gloves of the invention effectively preserve and maintain the wearer's protective skin barrier during use.

Example 10

Flaking Data

Then subjects' hands were evaluated for both fine flaking and coarse flaking, the measurements being obtained using D-Squame™ Skin Sampling Discs for skin smoothness and flakiness. Desquamation (e.g., peeling, flaking or scaliness) refers to the detachment of cells from the epithelium surface. Dr flaking is measured by D'suame and computerized image analysis. The desquamation index (DI) was used to measure overall dryness, and is calculated by the integration of the percent area covered by scales and their thickness distribution. DI is an indicator of the status of stratum corneum (SC) hydration. The results are summarized in the following table:

TABLE 4

| Percent Change in Flakiness/Dryness | | |
|---|---|---|
| | Test Article A | Test Article B (control) |
| Fine flaking (% difference) | −34% | −23.1% |
| Coarse flaking (% difference) | −58% | −60% |

TABLE 4-continued

Percent Change in Flakiness/Dryness

|  | Test Article A | Test Article B (control) |
|---|---|---|
| Overall dryness (% difference) | −41.98% | −40.0 |

As seen in the above data, subjects reported a 34% reduction in fine flaking and a 58% reduction on coarse flaking as a result of wearing gloves prepared in accordance with the invention as compared to untreated gloves. Fine flaking values are regarded as desquamation potential. Thus, the gloves treated according to the invention provided better and durable emollient properties as compared to untreated gloves.

II. Clinical Self-Assessment Study

Thirty subjects, including both males and females, were used for the study. The subjects refrained from using any lotions, creams or gels for a period of twenty-four hours prior to the study. The subjects' hands were washed under observation and then provided with the treated nitrile examination gloves of the invention to be worn for six successive 15-minute periods on one hand. A five-minute rest period occurred between each 15 minute wear period. The hands wearing the glove were alternated from left to right hands to eliminate positional bias. Questionnaires were administered before and after each 90 minute wear period. Twenty-four hours following the glove-wearing, the subjects were questioned.

Example 11

Skin Moisture

The subjects evaluated skin moisture levels on a scale of 1 through 5 (level 1 indicating extremely dry skin/not moist at all, and level 5 indicating very moist). Percent change in moisture level was measured at three main times: before use of glove, after use of glove during study, and 24 hours after use of gloves, with percentages calculated from the total of each evaluation score category. The results are set forth in the following table:

TABLE 5

Skin Moisture Level Results

| Level | Before | After | After 24 Hours |
|---|---|---|---|
| 1 | 40% | 0% | 4% |
| 2 | 20% | 0% | 26% |
| 3 | 33% | 20% | 70% |
| 4 | 7% | 43% | 0% |
| 5 | 0% | 37% | 0% |

As can be seen from the above data, 100% of the subjects experienced improvement in skin moisture. 63% of the subjects experienced significant improvement, i.e., improvement difference of at least two levels). Gloves prepared according to the invention also produced a lasting effect capturing and maintaining moisture level after 24 hours.

Example 12

Redness/Irritation

The subjects evaluated skin redness and irritation levels on a scale of 1 through 5 (level 1 indicating no irritation/redness, and level 5 indicating very red or irritated). Percent change in redness/irritation level was measured at three main times: before use of glove, after use of glove during study, and 24 hours after use of gloves, with percentages calculated from the total of each evaluation score category. The results are set forth in the following table:

TABLE 6

Skin Redness and Irritation Level Results

| Level | Before | After | After 24 Hours |
|---|---|---|---|
| 1 | 50% | 94% | 87% |
| 2 | 30% | 6% | 10% |
| 3 | 20% | 0% | 3% |
| 4 | 0% | 0% | 0% |
| 5 | 0% | 0% | 0% |

As can be seen from the above data, the subjects experienced a significant reduction in redness and irritation. 93% of subjects reported that redness and irritation had diminished to level 1, corresponding to the complete absence of irritation or redness.

Example 13

Skin Chapping

The subjects evaluated chapped skin levels on a scale of 1 through 5 (level 1 indicating no chapping, and level 5 indicating very chapped). Percent change in chapping level was measured at three main times: before use of glove, after use of glove during study, and 24 hours after use of gloves, with percentages calculated from the total of each evaluation score category. The results are set forth in the following table:

TABLE 7

Skin Chapping Level Results

| Level | Before | After | After 24 Hours |
|---|---|---|---|
| 1 | 17% | 70% | 80% |
| 2 | 36% | 13% | 7% |
| 3 | 30% | 17% | 10% |
| 4 | 17% | 0% | 3% |
| 5 | 0% | 0% | 0% |

As can be seen from the above data, the subjects experienced a 67% reduction in chapped skin level.

Example 14

Flaking

The subjects evaluated skin flaking levels on a scale of 1 through 5 (level 1 indicating no flaking at all, and level 5 indicating very flaky). Percent change in flaking level was measured at three main times: before use of glove, after use of glove during study, and 24 hours after use of gloves, with percentages calculated from the total of each evaluation score category. The results are set forth in the following table:

TABLE 8

Skin Flaking Level Results

| Level | Before | After | After 24 Hours |
|---|---|---|---|
| 1 | 60% | 83% | 86% |
| 2 | 20% | 7% | 7% |
| 3 | 20% | 7% | 7% |
| 4 | 0% | 3% | 0% |
| 5 | 0% | 0% | 0% |

As can be seen from the above data, the subjects experienced a reduction in skin flaking level.

Example 15

Softness

The subjects evaluated skin softness, smoothness and suppleness levels on a scale of 1 through 5 (level 1 indicating not at all soft, smooth supple, and level 5 indicating very soft, smooth, supple). Percent change in levels was measured at three main times: before use of glove, after use of glove during study, and 24 hours after use of gloves, with percentages calculated from the total of each evaluation score category. The results are set forth in the following table:

TABLE 9

Skin Softness Level Results

| Level | Before | After | After 24 Hours |
|---|---|---|---|
| 1 | 13% | 0% | 3% |
| 2 | 37% | 0% | 14% |
| 3 | 44% | 10% | 52% |
| 4 | 3% | 41% | 24% |
| 5 | 3% | 49% | 7% |

As can be seen from the above data, the subjects experienced an 87% increase in skin smoothness, softness and supple feel level.

Example 16

Itching

The subjects evaluated skin itch level on a scale of 1 through 5 (level 1 indicating not at all itchy, and level 5 indicating very itchy). Percent change in itchiness level was measured at three main times: before use of glove, after use of glove during study, and 24 hours after use of gloves, with percentages calculated from the total of each evaluation score category. The results are set forth in the following table:

TABLE 10

Skin Itching Level Results

| Level | Before | After | After 24 Hours |
|---|---|---|---|
| 1 | 70% | 97% | 93% |
| 2 | 20% | 3% | 0% |
| 3 | 10% | 0% | 7% |
| 4 | 0% | 0% | 0% |
| 5 | 0% | 0% | 0% |

Of the 30% of subjects with some level of itching, had 89% reduction in skin itching level.

Example 17

Skin Texture

The subjects evaluated skin texture levels on a scale of 1 through 5 (level 1 indicating not at all firm, and level 5 indicating very firm). Percent change in skin firmness level was measured at three main times: before use of glove, after use of glove during study, and 24 hours after use of gloves, with percentages calculated from the total of each evaluation score category. The results are set forth in the following table:

TABLE 11

Skin Firmness Level Results

| Level | Before | After | After 24 Hours |
|---|---|---|---|
| 1 | 0% | 7% | 17% |
| 2 | 13% | 7% | 7% |
| 3 | 54% | 36% | 59% |
| 4 | 23% | 30% | 14% |
| 5 | 10% | 20% | 3% |

As can be seen from the above data, the subjects reported that the gloves of the invention produced firmer skin

Example 18

Visible Fine Wrinkles

The subjects evaluated visible signs of fine wrinkle levels on a scale of 1 through 5 (level 1 indicating no visible fine wrinkles, and level 5 indicating very visible fine wrinkles). Percent change in visible skin fine wrinkling level was measured at three main times: before use of glove, after use of glove during study, and 24 hours after use of gloves, with percentages calculated from the total of each evaluation score category. The results are set forth in the following table:

TABLE 12

Skin Fine Wrinkle Visibility Results

| Level | Before | After | After 24 Hours |
|---|---|---|---|
| 1 | 20% | 10% | 28% |
| 2 | 13% | 7% | 17% |
| 3 | 20% | 27% | 42% |
| 4 | 27% | 33% | 10% |
| 5 | 20% | 23% | 3% |

As can be seen from the above data, the subjects reported a significant reduction (−50%) of visible fine wrinkles.

Synthetic Surgeon's Gloves

Gloves prepared in accordance with the invention were clinically evaluated for a variety of skin properties. In each of the following examples, two types of gloves were tested. Test Article A was a synthetic Non-Latex Polyisoprene Powder-free Surgical Glove with Lotion (Esteem™) prepared according to the invention using the coating composition of Example 5, Formula 4 (TSC 4.10%) and process similar to that of Example 2A. Control Test Article B, the comparator glove, was a Non-Latex Polyisoprene Powder-free Surgical Glove (Esteem™) (available from Cardinal Health, Inc., Dublin, Ohio). Twenty-nine subjects, male and female, were pre-screened for dry skin on the hands following a 36-48 hour "wash out" period, in which the hands were washed daily with Neutrogena® Glycerin Bar and without the use of any moisturizing products on their hands. Twenty-five subjects were selected varying in age from 27 to 59 years. No adverse events were reported during the study.

Each subject was equilibrated in a controlled environment for thirty minutes prior to baseline measurements. Baseline measurements were taken of the subjects' hands corresponding to the various testing methods to be applied: NOVA™ meter readings (NOVA™ DPM 9003™, NOVA Technology Corporation, Portsmouth, N.H.) for skin surface moisturization; TEWL (transepidermal water loss) measurements (TewaMeter™ TM 210 Courage+Khazaka Electronic GmbH, Koln, Germany) for barrier function; Cutometer™ MPA 580 (Courage+Khazaka Electronic GmbH, Koln, Germany) meaurements to assess skin elasticity; Replica® locators (Cuderm, Dallas, Tex.) and SILFLO™ Resin, from Flexico, Davis Healthcare Services, Ltd., Hertz, England) for measurement of fine lines and wrinkles.

Each of the twenty-five subjects were given the test glove to wear on one hand and a control glove for the contra hand for three one-hour wear periods. Two five minute rest periods were given between the first two one-hour periods. After the final one-hour wear period, the subjects were equilibrated again in a controlled environment room for thirty minutes. All measurements taken at the baseline period were taken again (final measurements).

Example 19

Comparative Data—Moisturization

Baseline and final NOVA™ meter readings (NOVA™ DPM 9003™, NOVA Technology Corporation, Portsmouth, N.H.) were measured for both test Articles to evaluate skin surface moisturization. The measurements were used to calculated percent change. The results are summarized in the following table:

TABLE 13

NOVA Percent Change

|  | Test Article A | Test Article B (control) |
|---|---|---|
| % Change | 9.74% | 6.34% |

As can be seen from the above results, Test Article A of the invention produced a 54% greater increase in skin moisture from baseline to final measurement readings as compared to Test Article B.

Example 20

Comparative Data—Skin Barrier Maintenance

Transepidermal water loss (TEWL) baseline and final measurements for each Test Article were taken using a TewaMeter™ TM 210 Courage+Khazaka Electronic GmbH, Koln, Germany) in order to evaluate skin barrier function. Percent change was calculated from the measurements, the results of which are summarized in the following table:

TABLE 14

TEWL Percent Change

|  | Test Article A | Test Article B (control) |
|---|---|---|
| % Change | 4.87 | 12.37 |

As can be seen from the above results, Test Article B caused an increase in transepidermal water loss of 154% over Test Article A of the invention from baseline to final readings. This indicates that significantly less skin barrier function deterioration occurs in the glove of the invention as compared to untreated gloves.

Example 21

Comparative Data—Elasticity

Two elasticity parameters were measured by Cutometer™ MPA 580 (Courage+Khazaka Electronic GmbH, Koln, Germany) for each of Test Article A to Test Article B. The first parameters is R6, which is a ratio of viscoelastic deformation (Uv) to elastic deformation (Ue), measuring overall elasticity, associated with viscoelastic parameters independent of skin thickness. The second parameter is Ue, which measures elastic deformation, associated with immediate distension. Percent change of R6 and Ue were calculated, and the results are summarized in the following tables:

TABLE 15

R6 Percent Change

|  | Test Article A | Test Article B (control) |
|---|---|---|
| % Change | −1.28% | 12.35% |

TABLE 16

Ue Percent Change

|  | Test Article A | Test Article B (control) |
|---|---|---|
| % Change | 31.45% | 11.15% |

The above data demonstrates a decrease in R6 value for Test Article A, as opposed to an increase for control Test Article B. As can also be seen, Test Article A produced an Ue increase 2.8 times greater than the increase produced by test Article B. Collectively, the decrease in R6 value and corresponding increase in Ue value demonstrate that after wearing the gloves prepared in accordance with the invention, the wearer's skin exhibits improved skin elasticity properties as compared to untreated gloves.

Example 22

Comparative Data—Visible Lines and Creases

Replica® locators (Cuderm, Dallas, Tex.) and SILFLO™ Resin, from Flexico, Davis Healthcare Services, Ltd., Hertz, England) were used to measure fine lines and wrinkles on the skin surface of the subjects. The data has been summarized and is set forth in the following table:

TABLE 17

Comparative Replica Image Analysis
of Polyisoprene Surgical Glove

| | Test Article A | Test Article B |
|---|---|---|
| FNUM initial | 0.946 | 0.998 |
| FNUM final | 1.028 | 0.891 |
| FNUM change | 0.081 | 0.106 |
| P(t) | 0.1457 | 0.0333 |

The above data demonstrates that Test Article B produced significant increase in lines and wrinkles as measured by FNUM values as compared to test Article A. In conclusion, lotioned gloves prepared according to the invention exhibit significantly reduced fine line and wrinkle appearance as compared to gloves without lotion.

The above clinical data demonstrates the improvements associated with the wearing of gloves of the invention. More specifically, gloves prepared in accordance with the invention provide collective therapeutic enhancements to the wearer's skin. These therapeutic enhancements include short and long term skin moisture retention, reductions in irritation and redness, flaking, maintenance of skin barrier function, and noticeable skin softness. These attributes can be provided to the user's hands without compromising the functionality of the gloves critical to their use.

INDUSTRIAL APPLICABILITY

The invention provides a coating composition for the skin-contacting surfaces of elastomeric articles which provide beneficial therapeutic skin treatment to the wearer's skin. The advantages afforded by the invention are particularly useful in elastomeric articles which are associated with prolonged periods of wear, such as surgical gloves, where deterioration of beneficial skin properties can occur as a result of such prolonged wear. Elastomeric articles made according to the invention can be used in a variety of contexts in addition to the medical field, such as food preparation or cosmetic usage environments. Accordingly, gloves made according to the invention not only reduce the adverse effects on the wearer's skin typically associated with elastomeric gloves worn for long periods of time, but improve the condition of the wearer's skin.

The invention has been described herein above with reference to various and specific embodiments and techniques. It will be understood by one of ordinary skill in the art, however, that reasonable variations and modifications of such embodiments and techniques can be made without substantially departing from either the spirit or scope of the invention as defined by the claims set forth below.

What is claimed is:

1. An elastomeric article comprising:
   an elastomeric layer having a skin-contacting elastomeric surface; and
   a coating composition provided directly on substantially the entire skin-contacting elastomeric surface of said elastomeric layer, said coating composition being in a dry state and comprising:
   a) at least one polyhydric alcohol moisturizer, wherein polyhydric alcohol moisturizers are present in a combined amount ranging from about 30% to about 37% of the total solids content of the coating composition; and
   b) at least one alphahydroxy lactone in an amount ranging from about 5% to about 12% of the total solids content of the coating composition;
   wherein said composition is water-soluble and hydratable upon contact with skin.

2. The elastomeric article according to claim 1 wherein the elastomeric layer is composed of natural rubber.

3. The elastomeric article according to claim 1 wherein the elastomeric layer is composed of synthetic rubber.

4. The elastomeric article according to claim 3 wherein the synthetic rubber is nitrile rubber.

5. The elastomeric article according to claim 3 wherein the synthetic rubber is polyisoprene.

6. The elastomeric article according to claim 1 wherein said article is an examination glove.

7. The elastomeric article according to claim 1 wherein said article is a surgeon's glove.

8. The elastomeric article according to claim 1 wherein said at least one polyhydric alcohol moisturizer comprises pantothenol in provitamin B form.

9. The elastomeric article of claim 8, wherein pantothenol is present in an amount ranging from about 10% to about 13% of the total solids content of the coating composition.

10. The elastomeric article according to claim 1 wherein said at least one alphahydroxy lactone is gluconolactone.

11. The elastomeric article according to claim 10 wherein said gluconolactone is D-glucono-1,5-lactone.

12. The elastomeric article according to claim 1 wherein said at least one polyhydric alcohol moisturizer comprises pantothenol in combination with at least one of glycerin and sorbitol.

13. The elastomeric article according to claim 1 wherein said coating composition further comprises a water-soluble film-forming polymer.

14. The elastomeric article according to claim 13 wherein said water-soluble film-forming polymer comprises chitosan.

15. The elastomeric article according to claim 1, wherein the coating composition further comprises a hydration promoter.

16. The elastomeric article according to claim 1, wherein the coating composition further comprises a plasticizer.

17. The elastomeric article according to claim 1, wherein prior to application to the elastomeric article, said coating composition comprises:
   a) water-soluble polyhydric alcohol moisturizer present in an amount up to about 3.00% by weight of the total composition; and
   b) alphahydroxy lactone present in an amount ranging from about 0.10% to about 3.00% by weight of the total composition.

18. The elastomeric article of claim 1, wherein one of the at least one polyhydric alcohol moisturizers comprises glycerin in an amount ranging from about 5% to about 7% of the total solids content of the coating composition.

19. The elastomeric article of claim 1, wherein one of the at least one polyhydric alcohol moisturizers comprises sorbitol in an amount ranging from about 15% to 19% of the total solids content of the coating composition.

20. An examination glove comprising:
   an elastomeric layer having a skin-contacting elastomeric surface; and
   a coating composition provided directly on substantially the entire skin-contacting elastomeric surface of said elastomeric layer; said coating composition being in a dry state and comprising:
   a) at least one polyhydric alcohol moisturizer, wherein polyhydric alcohol moisturizers are present in a combined amount ranging from about 30% to about 37% of the total solids content of the coating composition; and b) at least one alphahydroxy lactone in an amount ranging from about 5% to about 12% of the total solids content of the coating composition;
wherein said composition is water-soluble and hydratable upon contact with skin.

21. The examination glove of claim 20, wherein one polyhydric alcohol moisturizer of said at least one polyhydric alcohol moisturizer is present in an amount ranging from about 5% to about 19% of the total solids content of the coating composition.

22. A surgeon's glove comprising:
an elastomeric layer having a skin-contacting elastomeric surface; and
a coating composition provided directly on substantially the entire skin-contacting elastomeric surface of said elastomeric layer; said coating composition being in a dry state and comprising:
a) at least one polyhydric alcohol moisturizer, wherein polyhydric alcohol moisturizers are present in a combined amount ranging from about 30% to about 37% of the total solids content of the coating composition; and
b) at least one alphahydroxy lactone in an amount ranging from about 5% to about 12% of the total solids content of the coating composition;
wherein said composition is water-soluble and hydratable upon contact with skin.

23. The surgeon's glove according to claim 22, wherein said coating composition further comprises chitosan.

24. The surgeon's glove of claim 22, wherein one polyhydric alcohol moisturizer of said at least one polyhydric alcohol moisturizer is present in an amount ranging from about 5% to about 19% of the total solids content of the coating composition.

25. The surgeon's glove according to claim 24, wherein said coating composition further comprises chitosan.

26. An elastomeric article comprising:
an elastomeric layer having a skin-contacting elastomeric surface; and
a coating composition provided directly on substantially the entire skin-contacting elastomeric surface of said elastomeric layer, said coating composition being in a dry state and comprising:
a) at least one polyhydric alcohol moisturizer, wherein one polyhydric alcohol moisturizer of said at least one polyhydric alcohol moisturizer is present in an amount ranging from about 5% to about 19% of the total solids content of the coating composition, and wherein polyhydric alcohol moisturizers are present in a combined amount ranging from about 30% to about 37% of the total solids content of the coating composition; and
b) at least one alphahydroxy lactone in an amount ranging from about 5% to about 12% of the total solids content of the coating composition;
wherein said composition is water-soluble and hydratable upon contact with skin.

27. The elastomeric article according to claim 26 wherein the elastomeric layer is composed of natural rubber.

28. The elastomeric article according to claim 26 wherein the elastomeric layer is composed of synthetic rubber.

29. The elastomeric article according to claim 28 wherein the synthetic rubber is nitrile rubber.

30. The elastomeric article according to claim 28 wherein the synthetic rubber is polyisoprene.

31. The elastomeric article according to claim 26 wherein said article is an examination glove.

32. The elastomeric article according to claim 26 wherein said article is a surgeon's glove.

33. The elastomeric article according to claim 26 wherein said at least one polyhydric alcohol moisturizer comprises pantothenol in provitamin B form.

34. The elastomeric article of claim 33, wherein pantothenol is present in an amount ranging from about 10% to about 13% of the total solids content of the coating composition.

35. The elastomeric article according to claim 26 wherein said at least one alphahydroxy lactone is gluconolactone.

36. The elastomeric article according to claim 35 wherein said gluconolactone is D-glucono-1,5-lactone.

37. The elastomeric article according to claim 26 wherein said at least one polyhydric alcohol moisturizer comprises pantothenol in combination with at least one of glycerin and sorbitol.

38. The elastomeric article according to claim 26 wherein said coating composition further comprises a water-soluble film-forming polymer.

39. The elastomeric article according to claim 38 wherein said water-soluble film-forming polymer comprises chitosan.

40. The elastomeric article according to claim 26, wherein the coating composition further comprises a hydration promoter.

41. The elastomeric article according to claim 26, wherein the coating composition further comprises a plasticizer.

42. The elastomeric article according to claim 26, wherein prior to application to the elastomeric article, said coating composition comprises:
a) water-soluble polyhydric alcohol moisturizer present in an amount up to about 3.00% by weight of the total composition; and
b) alphahydroxy lactone present in an amount ranging from about 0.10% to about 3.00% by weight of the total composition.

43. The elastomeric article of claim 26, wherein one of the at least one polyhydric alcohol moisturizers comprises glycerin in an amount ranging from about 5% to about 7% of the total solids content of the coating composition.

44. The elastomeric article of claim 26, wherein one of the at least one polyhydric alcohol moisturizers comprises sorbitol in an amount ranging from about 15% to 19% of the total solids content of the coating composition.

* * * * *